(12) United States Patent
Burlina et al.

(10) Patent No.: US 8,761,476 B2
(45) Date of Patent: Jun. 24, 2014

(54) HYPERSPECTRAL IMAGING FOR DETECTION OF SKIN RELATED CONDITIONS

(71) Applicant: The Johns Hopkins University, Baltimore, MD (US)

(72) Inventors: Philippe M. Burlina, North Bethesda, MD (US); Amit Banerjee, Burtonsville, MD (US); Saurabh Vyas, Odenton, MD (US); Luis Garza, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 51 days.

(21) Appl. No.: 13/626,301

(22) Filed: Sep. 25, 2012

(65) Prior Publication Data

US 2013/0114868 A1 May 9, 2013

Related U.S. Application Data

(60) Provisional application No. 61/557,708, filed on Nov. 9, 2011.

(51) Int. Cl.
*G06K 9/00* (2006.01)

(52) U.S. Cl.
USPC ........................................................ 382/128

(58) Field of Classification Search
None
See application file for complete search history.

(56) References Cited

U.S. PATENT DOCUMENTS

| | | | |
|---|---|---|---|
| 5,782,770 A | 7/1998 | Mooradian et al. | |
| 6,640,130 B1 | 10/2003 | Freeman et al. | |
| 7,257,437 B2 | 8/2007 | Demos et al. | |
| 7,562,057 B2 | 7/2009 | Maggioni et al. | |
| 8,045,805 B2 | 10/2011 | Ramsay et al. | |
| 8,159,661 B2 | 4/2012 | Moshe et al. | |
| 2007/0073156 A1 | 3/2007 | Zilberman et al. | |
| 2007/0232930 A1 | 10/2007 | Freeman et al. | |
| 2008/0123097 A1 | 5/2008 | Muhammed et al. | |
| 2009/0318815 A1 | 12/2009 | Barnes et al. | |
| 2009/0326383 A1* | 12/2009 | Barnes et al. | 600/476 |
| 2010/0056928 A1 | 3/2010 | Zuzak et al. | |
| 2011/0052019 A1 | 3/2011 | Moshe | |

FOREIGN PATENT DOCUMENTS

WO 2008103918 8/2008

OTHER PUBLICATIONS

Nakariyakul, Songyot, and David Casasent. "Fusion algorithm for poultry skin tumor detection using hyperspectral data." Applied optics 46.3 (2007): 357-364.*
Moser, Gabriele, and Sebastiano B. Serpico. "Automatic parameter optimization for support vector regression for land and sea surface temperature estimation from remote sensing data." Geoscience and Remote Sensing, IEEE Transactions on 47.3 (2009): 909-921.*

* cited by examiner

*Primary Examiner* — Nirav G Patel
(74) *Attorney, Agent, or Firm* — Aisha Ahmad

(57) ABSTRACT

A method of detecting a skin condition may include employing a multiband hyperspectral sensor to obtain multi-spectral data, employing the multi-spectral data to map constitutive skin parameters to corresponding spectral signatures via a forward model that enables generation of a set of samples including a plurality of parameters mapped to a plurality of spectral signatures, utilizing the set of samples to employ machine learning to generate an inverse model to enable mapping of a spectral signature of skin of a patient to corresponding skin parameters, estimating constitutive skin parameters of the skin of the patient based on the inverse model, and determining a distribution of the constitutive parameters for one or more skin locations.

20 Claims, 8 Drawing Sheets

HYPERSPECTRAL IMAGING FOR DETECTION OF SKIN RELATED CONDITIONS

CROSS-REFERENCE TO RELATED APPLICATIONS

Figure 1:
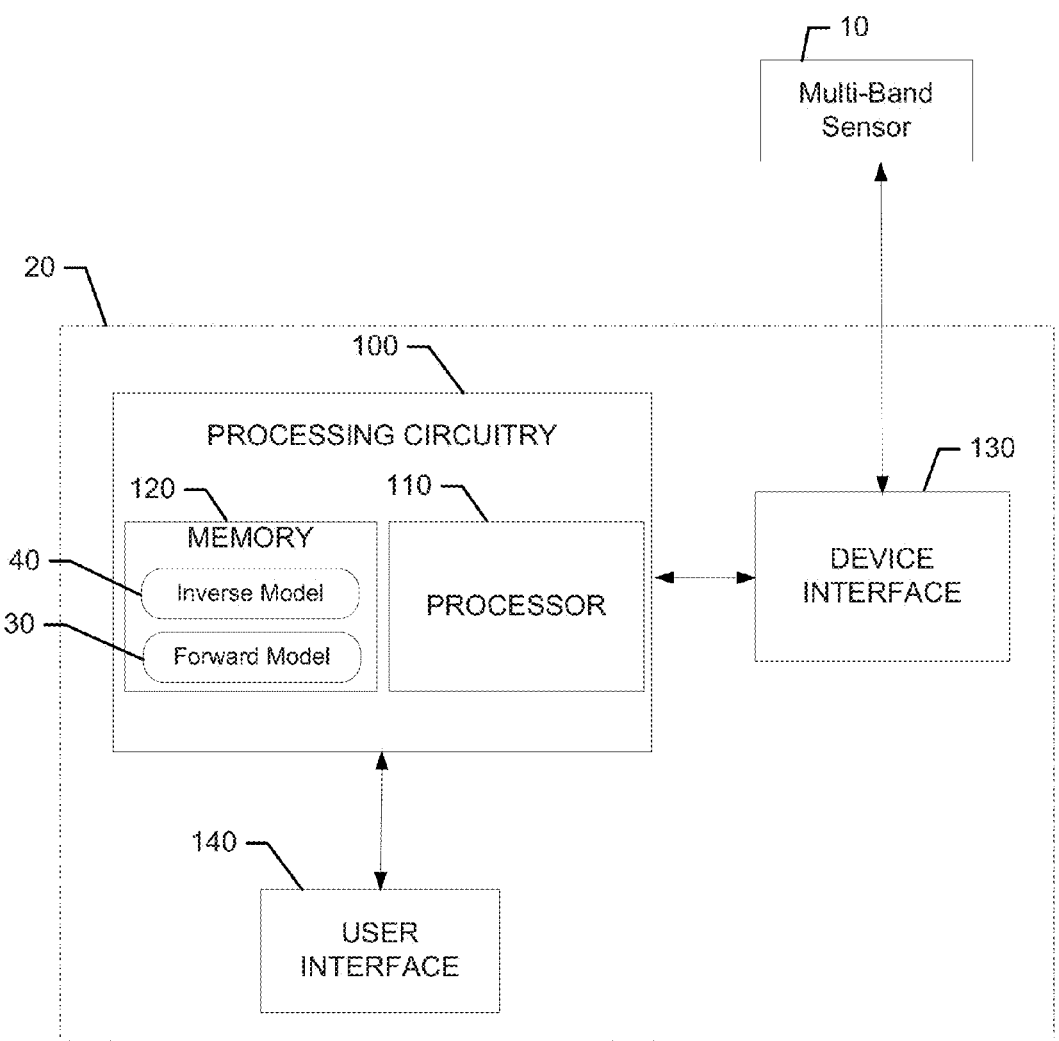

This application claims the benefit of U.S. Provisional Application No. 61/557,708 filed on Nov. 9, 2011, the entire contents of which are hereby incorporated herein by reference.

TECHNICAL FIELD

Exemplary embodiments of the present disclosure generally relate to detection of skin related ailments or conditions, and more specifically relate to employment of hyperspectral imaging for detection of conditions or ailments such as, but not necessarily limited to, skin cancer.

BACKGROUND

It is estimated that one person dies of melanoma, a severe form of skin cancer, every hour. Melanoma is characterized by rapid proliferation of melanocytes underneath the epidermis. During early stages of the disease, the tumor has a depth of about 1 mm and it can be excised completely with local surgery at a relatively high cure rate. However, the most common diagnostic for skin cancers, such as melanoma, is visual examination by a trained health care worker. Thus, the disease may often be missed or at least not draw attention while it is in its early stages. In the case of melanoma, this can mean the onset of distant metastasis—where the tumor moves to remote parts of the body through lymph vessels.

Recently, there has been significant interest in developing potent, efficient, and non-invasive techniques capable of detecting early signs of cancer in human skin. Though several technologies, including reflectance confocal microscopy, dermoscopy, etc. have emerged, they typically suffer from limitations associated with single band imaging. These techniques, or others like them, may also be employed for detection of other skin related ailments. Accordingly, it may be desirable to continue to develop additional methods and systems for minimally-invasive pre-screening for skin ailments such as cancers so that the methods and systems may be useable to achieve detection during the early stages of the diseases.

BRIEF SUMMARY OF SOME EXAMPLES

Accordingly, some example embodiments may enable the provision of a non-invasive approach to diagnosing skin cancers or other conditions related to changes in constitutive parameters of the skin. In this regard, some embodiments may enable a multi-band hyperpectral sensor to obtain images of the skin of a patient. From the data gathered, anomalies may be detected in the skin that may enable relatively early detection of skin cancers.

In one example embodiment, a detection system is provided. The detection system may include a multiband hyperspectral sensor configured to obtain multi-spectral data and a parametric analyzer including processing circuitry. The processing circuitry may be configured to employ the multi-spectral data to map constitutive skin parameters to corresponding spectral signatures via a forward model that enables generation of a set of samples including a plurality of parameters mapped to a plurality of spectral signatures, utilize the set of samples to employ machine learning to generate an inverse model to enable mapping of a spectral signature of skin of a patient to corresponding skin parameters, estimate constitutive skin parameters of the skin of the patient based on the inverse model, and determine a distribution of the constitutive parameters for one or more skirt locations.

In another example embodiment, a method of detecting a skin condition is provided. The method may include employing a multiband hyperspectral sensor to obtain multi-spectral data, employing the multi-spectral data to map constitutive skin parameters to corresponding spectral signatures via a forward model that enables generation of a set of samples including a plurality of parameters mapped to a plurality of spectral signatures, utilizing the set of samples to employ machine learning to generate an inverse model to enable mapping of a spectral signature of skin of a patient to corresponding skin parameters, estimating constitutive skin parameters of the skin of the patient based on the inverse model, and determining a distribution of the constitutive parameters for one or more skin locations.

In another example embodiment, a computer program product comprising a computer-readable storage medium having computer-executable program code instructions stored therein is provided. The computer-executable program code instructions may include program code instructions for employing a multiband hyperspectral sensor to obtain multi-spectral data, employing the multi-spectral data to map constitutive skin parameters to corresponding spectral signatures via a forward model that enables generation of a set of samples including a plurality of parameters mapped to a plurality of spectral signatures, utilizing the set of samples to employ machine learning to generate an inverse model to enable mapping of a spectral signature of skin of a patient to corresponding skin parameters, estimating constitutive skin parameters of the skin of the patient based on the inverse model, and determining a distribution of the constitutive parameters for one or more skin locations.

BRIEF DESCRIPTION OF THE SEVERAL VIEWS OF THE DRAWING(S)

Figure 2A:
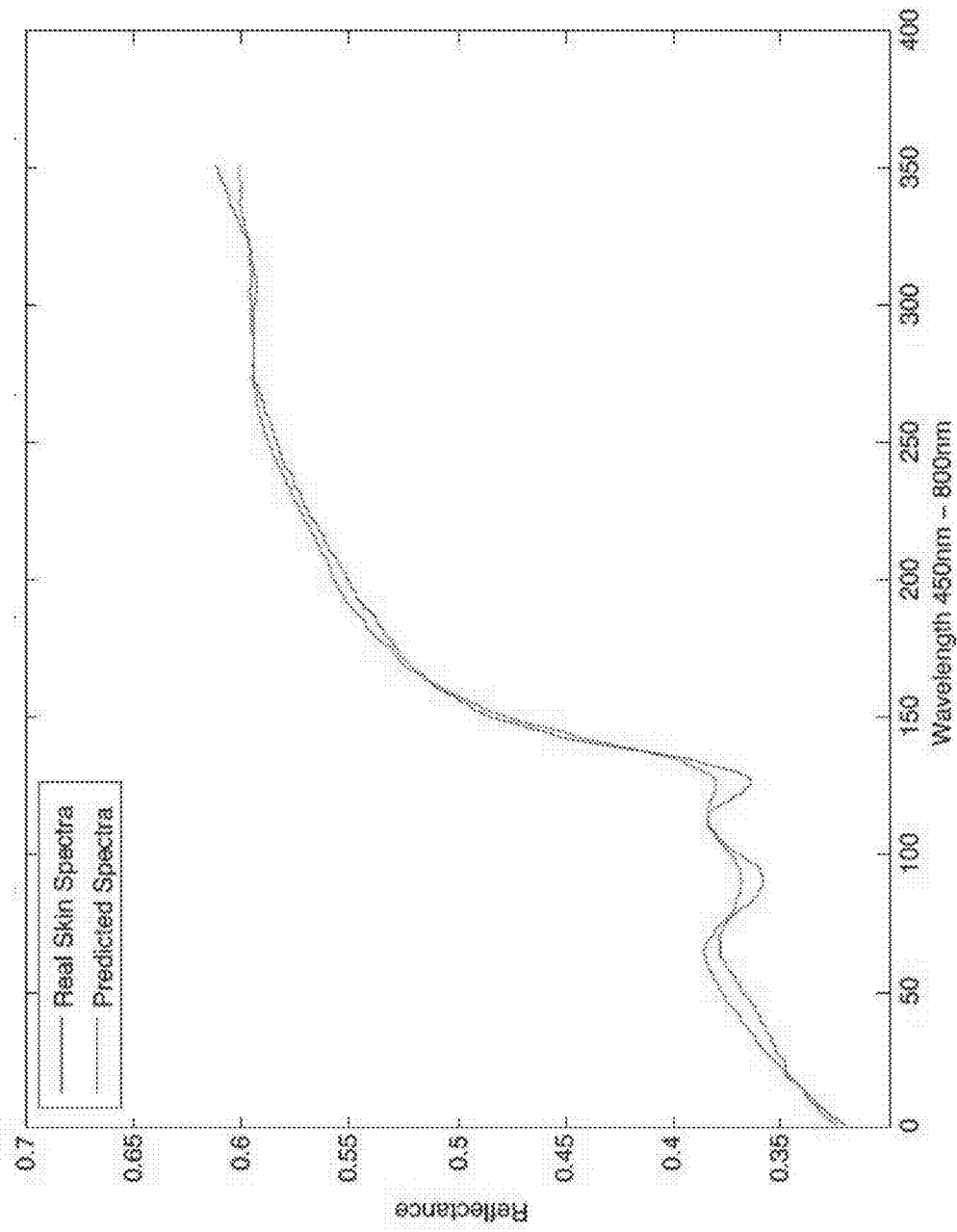
Figure 2B:
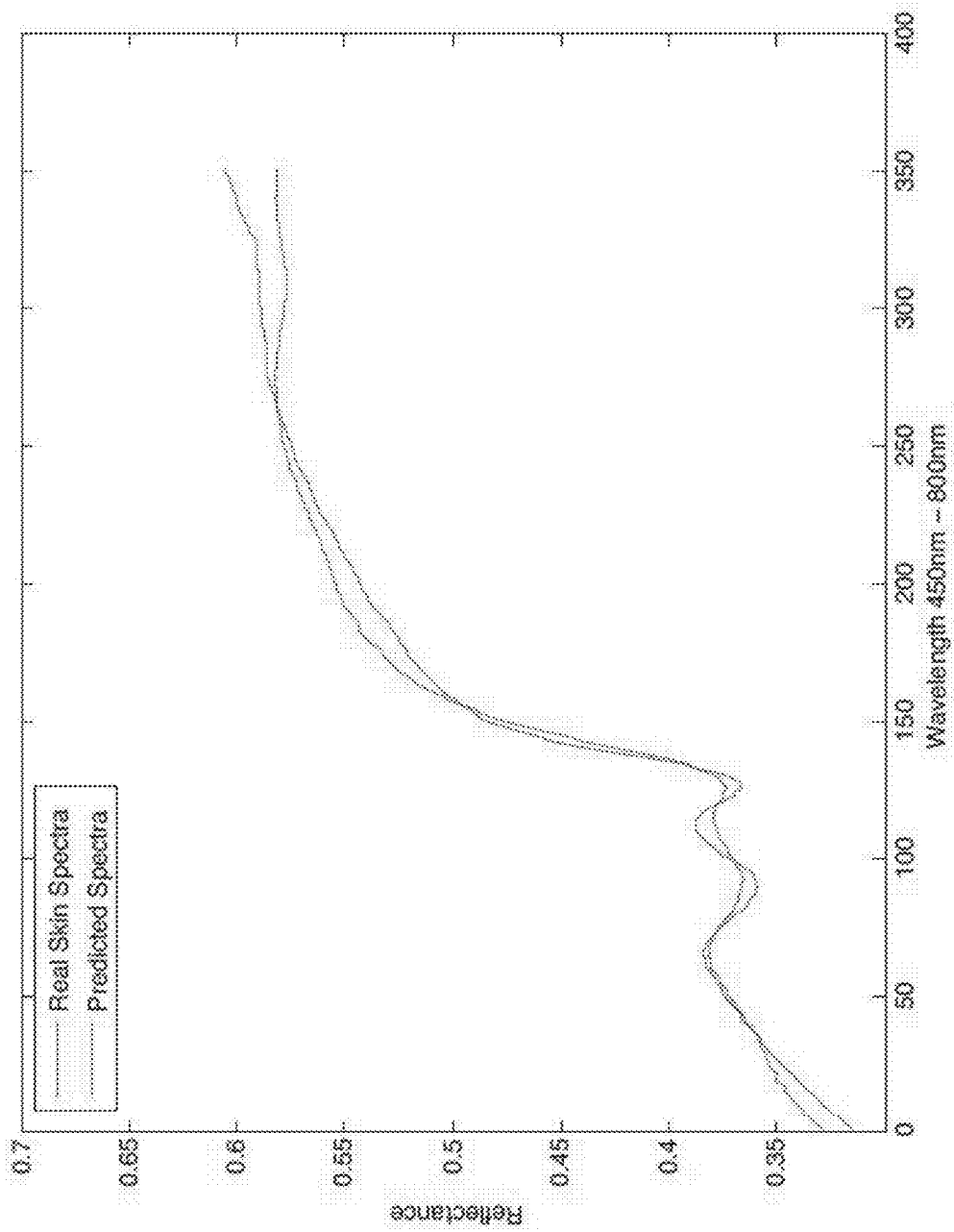
Figure 2C:
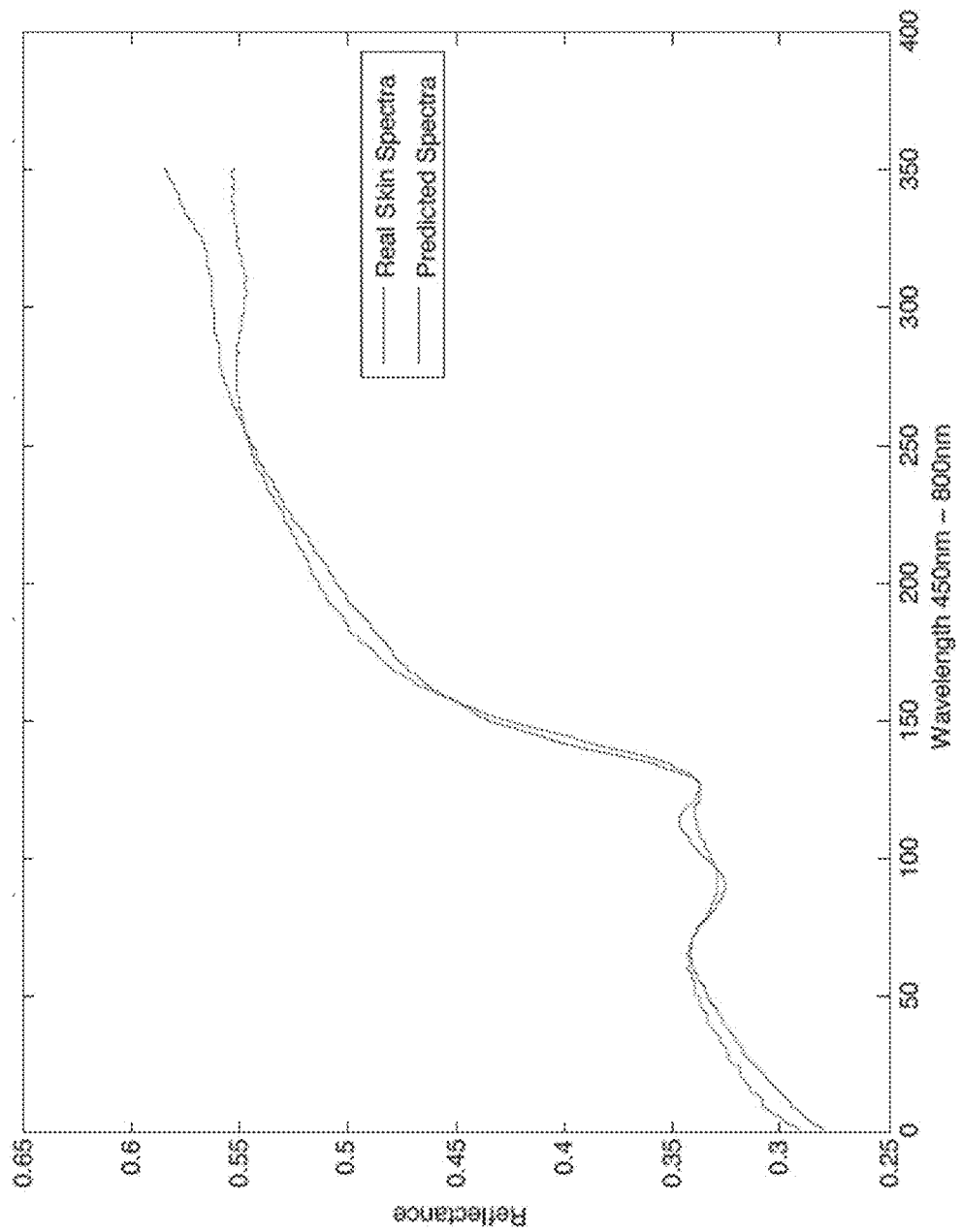
Figure 2D:
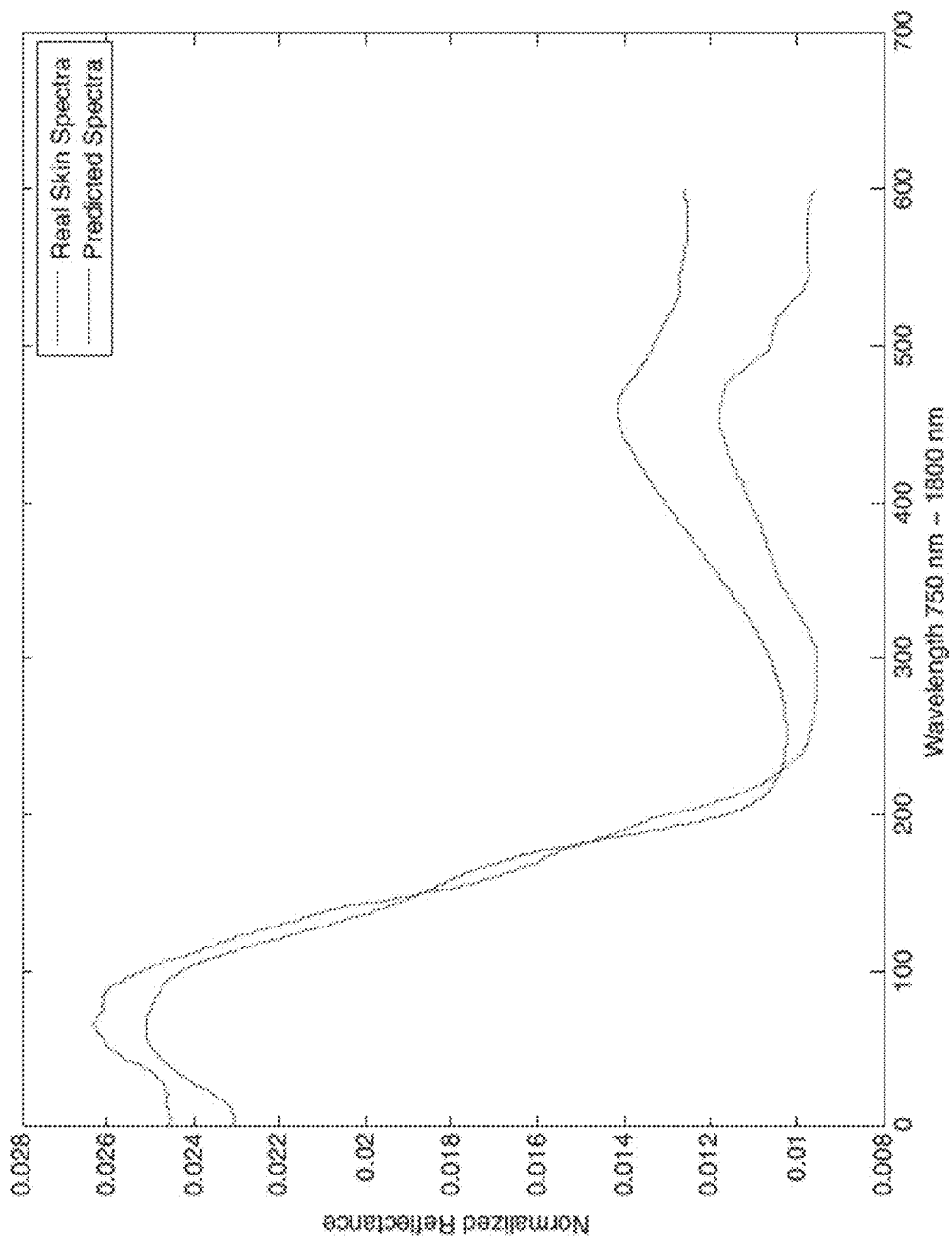
Figure 2E:
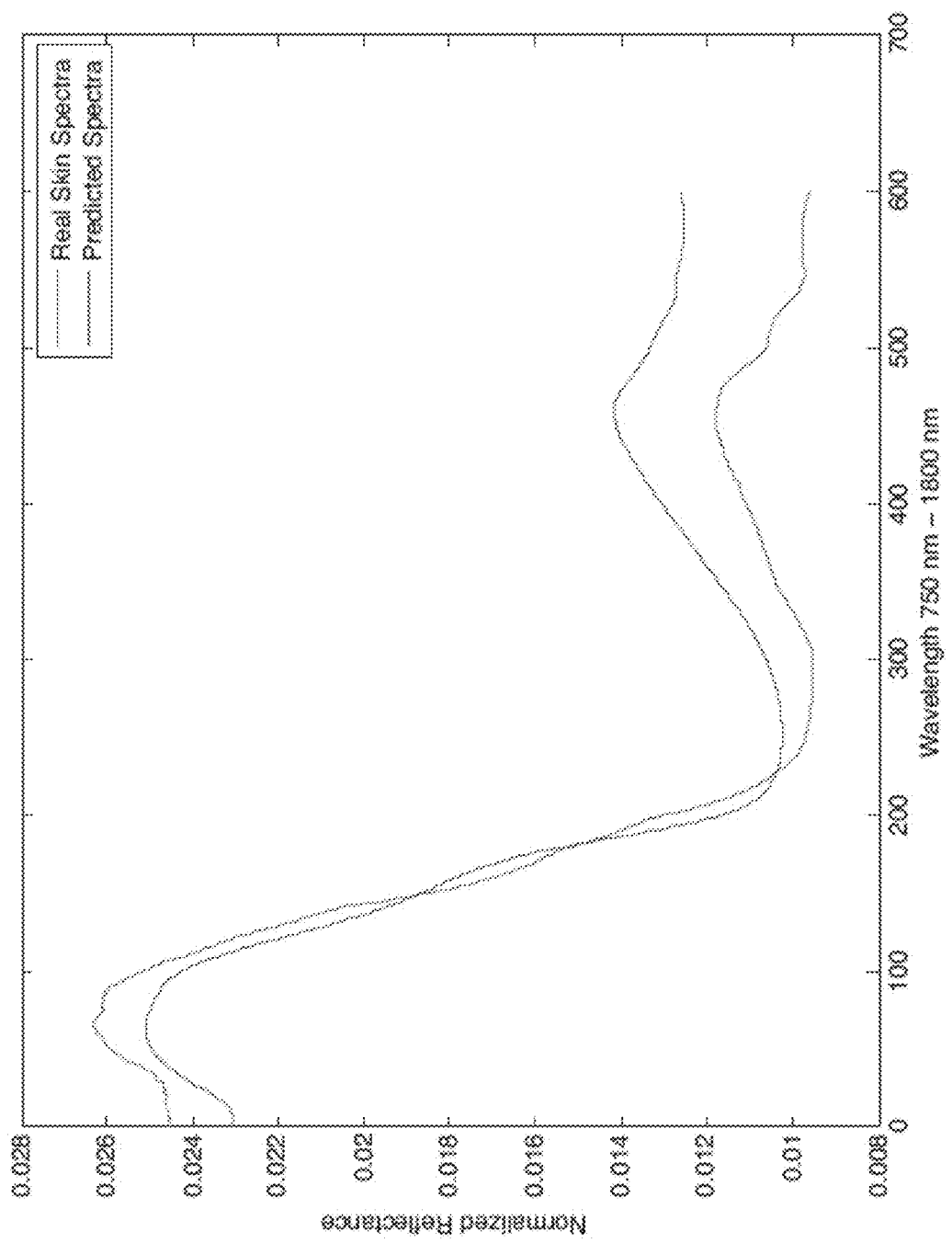
Figure 2F:
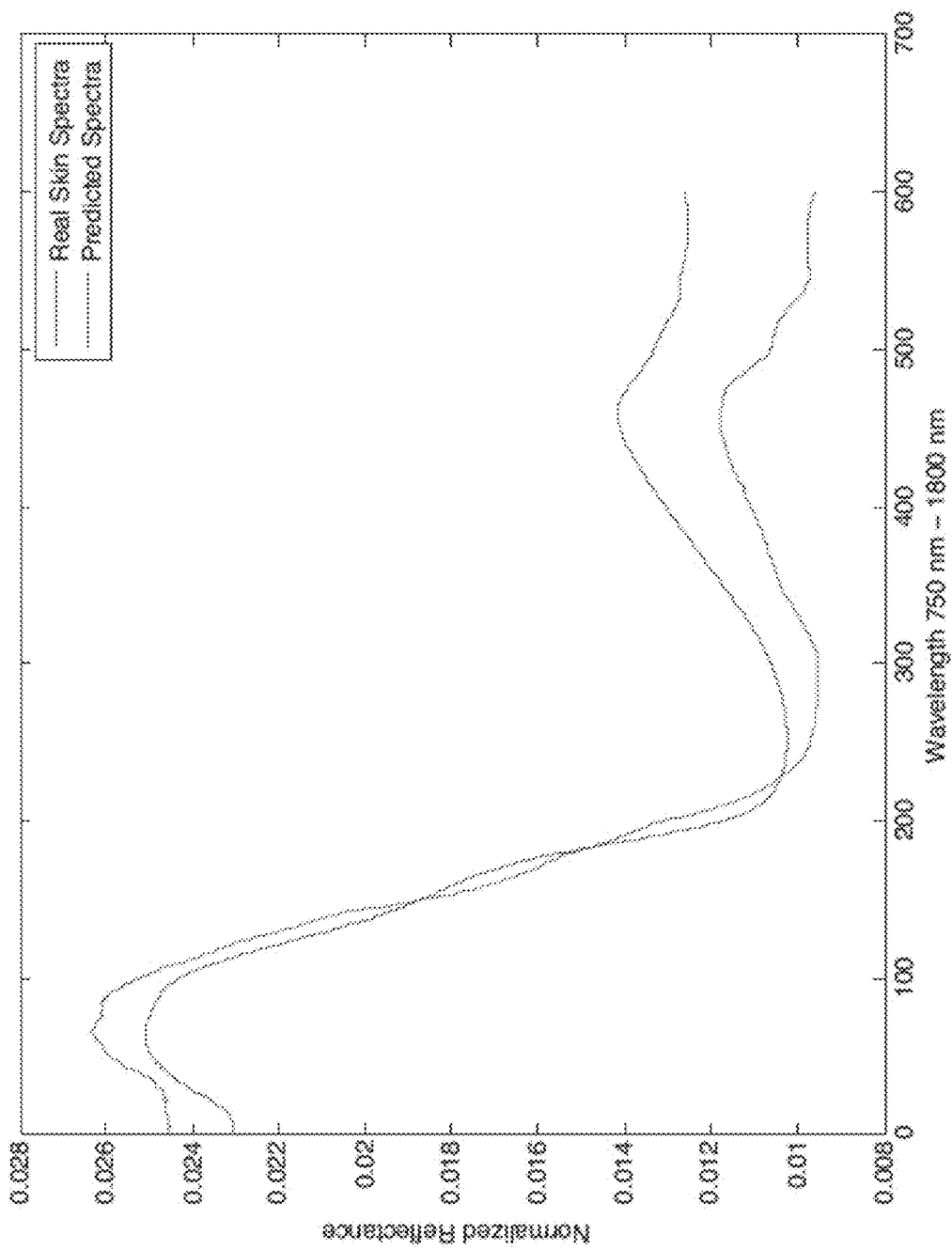
Figure 3:
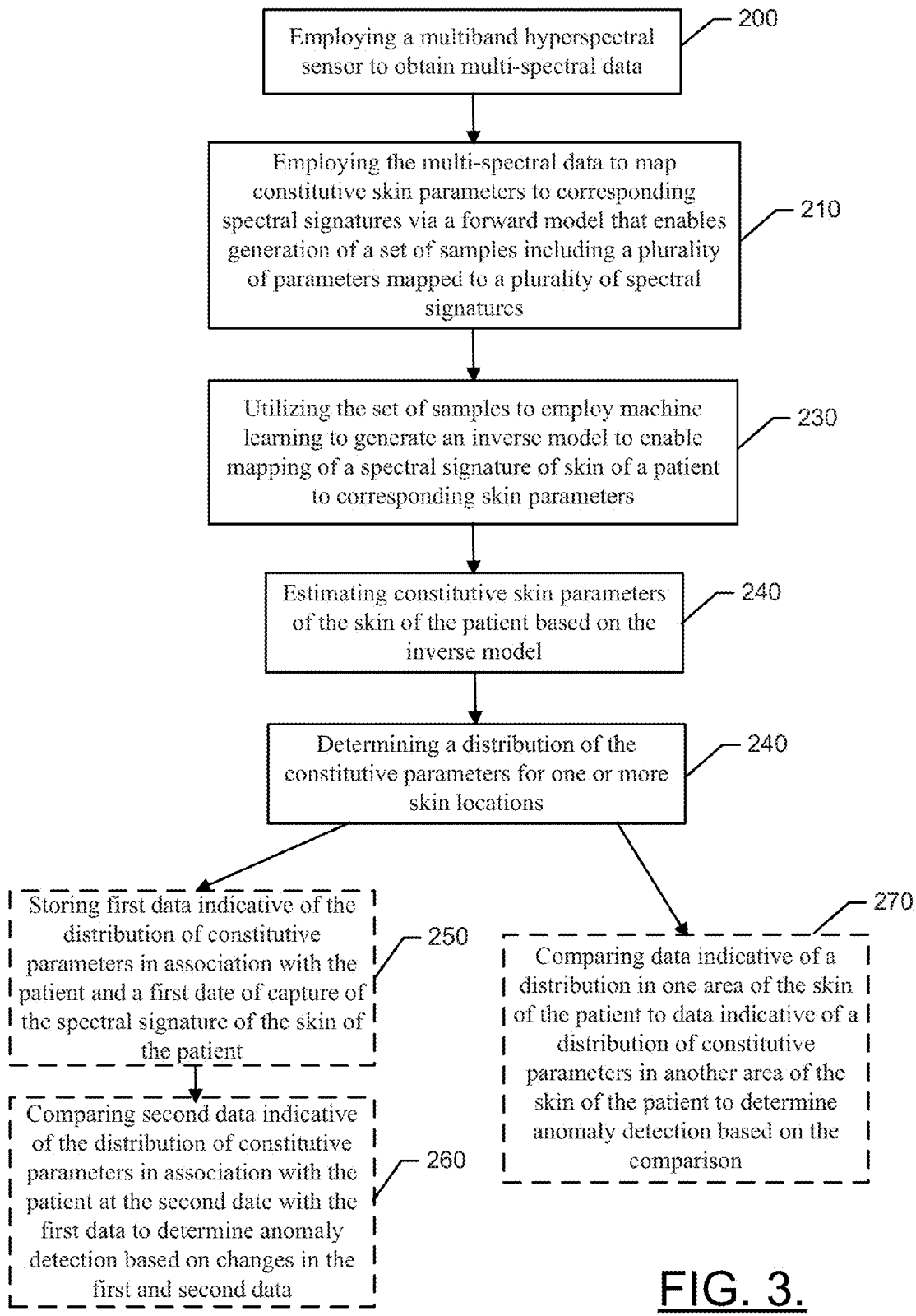

Having thus described the invention in general terms, reference will now be made to the accompanying drawings, which are not necessarily drawn to scale, and wherein:

FIG. 1 illustrates a block diagram showing one example of a detection system of an example embodiment;

FIG. 2, which includes FIGS. 2A, 2B, 2C, 2D, 2E and 2F, illustrates various example reflectance spectra achieved via the operation of an example embodiment; and FIG. 3 shows an exemplary block diagram of a method according to an example embodiment.

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

As indicated above, some example embodiments may enable the provision of a non-invasive approach to diagnosing skin cancers or other conditions related to changes in the skin. Moreover, example embodiments may enable relatively early detection using multi-band imaging techniques that employ, for example, hyperspectral imaging to quantitatively compute various biological parameters that make up the layers of human skin. The parameters of interest in connection with employing example embodiments may include melanosome collagen level, blood oxygenation, blood level, dermal depth, and/or subcutaneous tissue reflectance. Example embodiments may enable the use of longitudinal studies that track changes (e.g., changes in concentration) of these parameters, across various parts of the body, over a period of time. These studies may provide invaluable information relative to predicting the inception and spread of malignant tumors (such as melanoma). The ability to accurately estimate the skin constitutive parameters may also be useful in the pharmaceutical industry for quantifying the process of drug delivery through the skin, in the cosmetic industry for characterizing the delivery of lipids and measuring subtle levels of skin damage, and in the health care industry for providing a quantitative tool for characterizing the degree of skin aging. Some embodiments may therefore employ machine learning on skin reflectance data relative to the use of hyperspectral signatures collected in vivo and encompassing both males and females of various ethnicities. The biological parameters involved in tracing the growth and spread of various tissues such as cancer tissues can be predicted with relatively good accuracy based on the employment of example embodiments.

FIG. 1 illustrates a block diagram showing one example of a detection system of one example embodiment. In this example, the detection system is embodied as a computer controlled device. Thus, for example, the detection system may include a multi-band sensor 10 and a parametric analyzer 20. The multi-band sensor 10 may be an imaging device configured to obtain images of the skin of a subject. The data collectable by the multi-band sensor 10 may be captured remotely (e.g., without necessarily requiring any contact with the skin) by obtaining image data over any of a variety of spectra of interest. In some cases, some active transmission of radiation may be provided in order to measure reflectance or emittance characteristics of the skin over any of a plurality of spectra. In one embodiment, the multi-band sensor 10 may be embodies as or include a single pixel hyperspectral spectrometer. However, in other embodiments, some other imaging device may be employed such as, for example, a single image or video rate hyperspectral spectrometer. Examples of bands covered by the multi-band sensor 10 may include visible, near infrared (IR), short-wavelength (SWIR), mid-wavelength IR (MWIR), long-wavelength IR (LWIR), far IR and/or the like. IR frequencies may generally allow for deeper skin penetration relative to determination of characteristics such as reflectance and emittance.

The parametric analyzer 20 may be configured to receive and process data captured by the multi-band sensor 10 in order to generate results that may be used to diagnose various skin conditions. In some case, the parametric analyzer 20 may first be used to employ physics based forward modeling to map constitutive skin parameters (e.g., melanosome level, collagen blood oxygenation, blood level, dermal depth, and/or subcutaneous tissue reflectance) to spectral signals in a forward model 30. The forward model 30 may then be used to generate a relatively large sample size of sample exemplars (e.g., parameters and spectral signatures) of tuples. The sample data may be stored in a database (e.g., memory 120) for use in connection with enabling the parametric analyzer 20 to "learn" an inverse model 40 for use in mapping spectral signatures to skin parameters. The inverse model 40 may be generated by leveraging one or more machine learning regressions as described in greater detail below. The inverse model 40 may be used to estimate the constitutive parameters of the skin of a patient (subsequent to imaging of the patient's skin by the multi-band sensor 10) so that the distribution of the constitutive parameters for any skin locations that are determined to be at risk (e.g., areas with an irregular mole or moles) may be calculated.

Thus, for example, the parametric analyzer 20 may be employed first for forward mapping involving the generation of a map of constitutive skin parameters to corresponding spectral signatures to produce the forward model 30. Data indicative of the constitutive parameter space (e.g., melanosome, collagen, percent oxygenation, etc.) may be used in connection with forward mapping to generate a spectral signature. The parametric analyzer 20 may thereafter be employed to generate or learn the inverse model 40 to estimate constitutive parameters of the skin of a patent being analyzed to determine areas that may be at risk for inspection by a health care professional. In this regard, for example, a spectral signature of a patient may be used in connection with inverse mapping using the inverse model 40 to determine estimated constitutive parameters for the patient.

Of note, the same multi-band sensor may be used for obtaining data for generation of the forward model 30 and for analysis of a specific patient's imaging data. However, in some embodiments, a different multi-band sensor may be used to obtain one or more samples in a sample set and even a different parametric analyzer could also be used. The data (e.g., parameters and corresponding signatures) may then be provided to the parametric analyzer 20 for use with the multi-band sensor 10 to analyze data associated with the particular patient. Analysis and reporting regarding the particular patient's image data may be accomplished via real-time analysis, or may be accomplished by storing the patient's data and analyzing it at a later time.

As shown in FIG. 1, the parametric analyzer 20 may include or otherwise be in communication with processing circuitry 100 that is configurable to perform actions in accordance with example embodiments described herein. As such, for example, at least some of the functions attributable to the parametric analyzer 20 may be carried out by or otherwise instructed by the processing circuitry 100. The processing circuitry 100 may therefore provide the hardware for hosting software to configure the system for machine learning and machine vision analysis techniques consistent with example embodiments. Detection and delineation of skin conditions such as, for example, melanoma may then be accomplished using the processing circuitry 100.

The processing circuitry 100 may be configured to perform data processing, control function execution and/or other processing and management services according to an example embodiment of the present invention. In some embodiments, the processing circuitry 100 may be embodied as a chip or chip set. In other words, the processing circuitry 100 may comprise one or more physical packages (e.g., chips) including materials, components and/or wires on a structural assembly (e.g., a baseboard).

In an example embodiment, the processing circuitry 100 may include one or more instances of a processor 110 and memory 120 that may be in communication with or otherwise control a device interface 130 and, in some cases, a user interface 140. As such, the processing circuitry 100 may be embodied as a circuit chip (e.g., an integrated circuit chip) configured (e.g., with hardware, software or a combination of hardware and software) to perform operations described herein.

The user interface 140 (if implemented) may be in communication with the processing circuitry 100 to receive an indication of a user input at the user interface 140 and/or to provide an audible, visual, mechanical or other output to the user. As such, the user interface 140 may include, for example, a display, one or more buttons or keys (e.g., function buttons), and/or other input/output mechanisms (e.g., keyboard, microphone, speakers, cursor, joystick, lights and/or the like). The user interface 140 may display information indicating an identity or certain characteristics of a data set (e.g., including parameters and/or spectral signatures) being processed by the parametric analyzer 20. The characteristics of the data set may then be processed and information associated therewith may be presented on a display of the user interface 140 based on instructions executed by the processing circuitry 100 for the analysis of the data according to prescribed methodologies and/or algorithms. Moreover, in some cases, the user interface 140 may include options for selection of one or more reports to be generated based on the analysis of a given data set.

The device interface 130 may include one or more interface mechanisms for enabling communication with other external devices or internal functional components of the parametric analyzer 20 (e.g., the multi-band sensor 10, the forward model 30, the inverse model 40 and/or the like). In some cases, the device interface 130 may be any means such as a device or circuitry embodied in either hardware, or a combination of hardware and software that is configured to receive and/or transmit data from/to devices in communication with the processing circuitry 100.

In an exemplary embodiment, the memory 120 may include one or more non-transitory memory devices such as, for example, volatile and/or non-volatile memory that may be either fixed or removable. The memory 120 may be configured to store information, data, applications, instructions or the like for enabling the parametric analyzer 20 to carry out various functions in accordance with exemplary embodiments of the present invention. For example, the memory 120 could be configured to buffer input data for processing by the processor 110. Additionally or alternatively, the memory 120 could be configured to store instructions for execution by the processor 110. As yet another alternative, the memory 120 may include one or more databases that may store a variety of data sets indicative of patterns constitutive parameters, spectral signatures, processing algorithms and/or the like to be employed. Among the contents of the memory 120, applications may be stored for execution by the processor 110 in order to carry out the functionality associated with each respective application. In some cases, the applications may include directions for control of the parametric analyzer 20 to generate and/or employ the forward model 30, the inverse model 40, information and/or reports associated with analysis of patient data as described herein.

The processor 110 may be embodied in a number of different ways. For example, the processor 110 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 110 may be configured to execute instructions stored in the memory 120 or otherwise accessible to the processor 110. As such, whether configured by hardware or by a combination of hardware and software, the processor 110 may represent an entity (e.g., physically embodied in circuitry—in the form of processing circuitry 100) capable of performing operations according to embodiments of the present invention while configured accordingly. Thus, for example, when the processor 110 is embodied as an ASIC, FPGA or the like, the processor 110 may be specifically configured hardware for conducting the operations described herein. Alternatively, as another example, when the processor 110 is embodied as an executor of software instructions, the instructions may specifically configure the processor 110 to perform the operations described herein.

In an example embodiment, the processor 110 (or the processing circuitry 100) may be embodied as, include or otherwise control the parametric analyzer 20. As such, in some embodiments, the processor 110 (or the processing circuitry 100) may be said to cause each of the operations described in connection with the parametric analyzer 20 by directing the parametric analyzer 20 to undertake the corresponding functionalities responsive to execution of instructions or algorithms configuring the processor 110 (or processing circuitry 100) accordingly.

In an example embodiment, data captured in association with image scanning of the skin of a particular patient may be stored (e.g., in the memory 120) along with an indication of the date of the corresponding data gathering. Thereafter, data associated with one or more additional scans may also be stored in association with the particular patient's identity and the corresponding date of the gathering of the data. The storage of data over a plurality of different dates may enable a longitudinal study to be conducted in order to track the evolution of changes in the constitutive parameters of the patient's skin. Thus, for example, changes in the constitutive parameters of moles or other abnormal formations may be used to infer abnormal temporal evolution or spatial distribution of constitutive parameters that may suggest the development of a melanoma or other malignant cancerous formation. In some cases, temporal and spatial variations in constitutive parameters may be analyzed using a machine learning approach to infer abnormal cases.

In some example embodiments, the inverse model 40, and inverse mapping associated therewith, may be generated using a regression method that may be employed by the processing circuitry 100. In some cases, a support vector regression (SVR) may be employed. However, a k nearest neighbors (k-NN) regression or some other algorithm may be employed in other alternative embodiments. The spectral signatures may be directly analyzed by the processing circuitry 100 using a machine learning method such as, for example, a support vector learning method like support vector data description (SVDD) in order to infer areas of the skin that are abnormal when compared to other baseline areas in the same patient or individual. Accordingly, the processing circuitry 100 may be employed to perform patient-specific anomaly detection and diagnosis. In some embodiments, the memory 120 may store maps of constitutive parameters that are registered to each body of a respective patient or individual that is examined in order to allow assessments regarding the evolution of specific areas of the skin that may be at risk. Each time a new hyperspectral image is generated for a body already having registered data associated therewith, the new image and/or data may also be associated (e.g., automatically) with any prior data registered to the same patient or individual. In some cases, a prior analysis of the spectral bands may be performed in order to infer which are the most informative with regard to estimating constitutive parameters.

In an example embodiment, the processing circuitry 100 may be configured to employ a physics based forward model that maps an input vector space including biological parameters to an output vector space having the spectral components of the corresponding parameters:

$$F: p \to s$$

$p =$ [% Melanosome, % Collagen, % Blood Oxygenation]

$s = [\lambda_N, \ldots, \lambda_M], N = 451$ mm and $M = 800$ nm

In some embodiments, the forward mapping F may be derived from Kubelka-Munk theory, its corresponding analytical models and the Fresnal Equations. The reflectance spectra of human skin can be modeled with high accuracy by implementing the equations discussed above. Hyperspectral imaging may enable a multi-band reflectance spectra to be obtained from any in vivo skin sample. The skin spectra may then be used to infer underlying biological parameters by employing an inverse mapping:

$$G: s \to p$$

Thereafter, a regression based machine learning algorithm may be employed to characterize the desired inverse mapping, G. In some embodiments, as mentioned above, the processing circuitry 100 may be configured to employ SVP, k-NN, or some other regression for this purpose.

When employing SVR, a function $f(x)$ is sought such that f can fully describe the output to any input vector with minimal error. Following the SVR approach of some example embodiments, an input training set given by:

$$\{(x_1, y_1), \ldots, (x_n, y_n)\} \subset X \times \mathbb{R} \tag{1}$$

may be employed, where X signifies the vector space of the input pattern, e.g., ($X = \mathbb{R}$). The function $f(x)$ may then be sought such that there is at most $\epsilon$ error from the ground truth targets $y_i$, for each member of the training data. This may take a function form by:

$$f(x) = K\langle w, x \rangle + b, x \in X, b \in \mathbb{R} \tag{2}$$

where $K\langle w, x \rangle$ represents the kernel dot product in X. In addition, it may be desirable for the function $f$ to be as flat as possible based on an idea that errors may be tolerable as long as they do not exceed $\epsilon$. The flatness of f can be controlled by ensuring that the norm is minimized. In other words: $\|w\|^2 = K\langle w, w \rangle$. Therefore, a constrained optimization problem may be written as:

$$\text{minimize } \frac{1}{2}\|w\|^2 + C \sum_{i=q}^{l} (\zeta_i + \zeta_i^*) \tag{3}$$

$$\text{subject to} \begin{cases} y_i - K\langle w, x_i \rangle - b \leq \epsilon + \zeta_i \\ K\langle w, x_i \rangle + b - y_i \leq \epsilon + \zeta_i^* \\ \zeta_i \zeta_i^* \geq 0 \end{cases}$$

when $\zeta_i$ and $\zeta_i^*$ are slack variables to account for infeasible constraints on the problem as per the soft margin loss function. C is a constant and accounts for the balance between the flatness of f and the degree to which errors larger than $\epsilon$ are tolerated. The final step in the process may be to represent the problem as a Lagrangian function that needs to be minimized. The Lagrangian function may be constructed from the primal objective function and a dual set of variables. This can be seen by the following:

$$L := \frac{1}{2}\|w\|^2 + C \sum_{i=1}^{l} (\zeta_i + \zeta_i^*) + \tag{4}$$

$$\sum_{i=1}^{l} (\eta_i \zeta_i + \eta_i^* \zeta_i^*) - \sum_{i=1}^{l} \alpha_i(\epsilon + \zeta_i - y_i + K\langle w, x_i \rangle + b) -$$

$$\sum_{i=1}^{l} \alpha_i^*(\epsilon + \zeta_i^* + y_i - K\langle w, x_i \rangle - b)$$

where L is the Lagrangian and $\alpha_i$, $\alpha_i^*$, $\eta_i$, and $\eta_i^*$ are the Lagrangian multipliers. It can be shown that this function has a saddle point with respect to the primal objective function and the dual variables at the solution. Following conditions of optimality and the saddle point, the partial derivative of L with respect to w can be written as the "support vector expansion," given by:

$$w = \sum_{i=1}^{l} (\alpha_i - \alpha_i^*) x_i \tag{5}$$

$$f(x) = \sum_{i=1}^{l} (\alpha_i - a_i^*) \cdot K\langle w, x_i \rangle + b \tag{6}$$

which in other words assesses that w can be written as a linear combination of the training patterns, $x_i$. The complexity of the function's representation by support vectors, therefore, only depends on the number of support vectors, and not on the dimensionality of the input space, X. Finally, b can be computed using the Karush-Kuhn-Tucker (KKT) conditions, which state that at the point of the solution, the product between dual variables and constraints goes to zero.

When employing k-NN regression, the basic idea may be to classify or regress on objects in a testing set based on the closest training examples in the feature space. This algorithm used in regression mode may be simple in that the regression is based on linearly mixing the objects that stand amongst its k nearest neighbors of the test sample.

Closeness, as used herein, should be understood in relation to reflectance spectra of human skin. In the feature space in which some example embodiments operate may include, for example, three million reflectance spectra constructed by randomly generating and uniformly distributing the various skin parameters, as per F. Furthermore, the testing set may include skin spectra obtained in viva from hyperspectral imaging. Therefore, for this application, for each spectra in the training set, it may be desirable to find spectra from the training set that most closely match the shape of the testing spectra. This can be formally written as the spectral angle given by:

$$\Theta_{closest} = \cos^{-1} \frac{\vec{S}_{testing} \cdot \vec{S}_{training}}{\|\vec{S}_{testing}\| \|\vec{S}_{training}\|} \tag{7}$$

where $\vec{S}_{training}$ is a skin reflectance spectra from the training set contained within the feature space, and $\vec{S}_{testing}$ is the spectra for which classification is desired.

FIG. 2, which includes FIGS. 2A, 2B, 2C, 2D, 2E and 2F, illustrates various example reflectance spectra achieved via the operation of example embodiments. In this regard, FIG. 2 shows a plot of in vivo sample datasets plotted alongside its k-NN predicted closest neighbors for both the Vis region and the SWIR region of the EM spectrum, FIGS. 2A, 2B and 2C show reflectance spectra obtained from hyperspectral imaging (in the Vis region of the EM spectrum—450 nm to 800 nm) of three average in vivo samples plotted on the same screen as their predicted reflectance spectra from the computational model and machine learning. FIGS. 2D, 2E and 2F correspond to the same samples' spectra, except that they are in the SWIR region (750 nm to 1800 nm). The training dataset corresponding to each in vivo spectra is also plotted with the k-NN predicted closest neighbors, showing a relatively small distance (error) in the shape between the in vivo skin spectra and the predicted skin spectra. The fact that these are relatively close (e.g., have a small mean normalized distance and a small spectral angle error, demonstrates the ability of the model to describe in vivo skin spectra, based on biological parameters. Thus, biological parameters of interest can be predicted from the reflectance spectra.

Accordingly, inverse mapping may be employed to retrieve underlying skin parameters from a set of samples obtained in vivo via hyperspectral imaging. Knowledge of the underlying skin parameters (e.g., constitutive parameters) that are obtained temporally across various parts of the body can provide insight into the growth and progression of certain skin conditions such as malignant tumors. Thus, for example, via tracking changes to melaosomes over time in various parts of the body, insight may be gained regarding the development and/or progression of melanoma.

FIG. 3 is a flowchart of a method and program product according to an example embodiment of the invention. It will be understood that each block of the flowchart, and combinations of blocks in the flowchart, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory device of a user terminal and executed by a processor in the user terminal. As will be appreciated, any such computer program instructions may be loaded onto a computer or other programmable apparatus (e.g., hardware) to produce a machine, such that the instructions which execute on the computer or other programmable apparatus create means for implementing the functions specified in the flowchart block (s). These computer program instructions may also be stored in a computer-readable memory that may direct a computer or other programmable apparatus to function in a particular mariner, such that the instructions stored in the computer-readable memory produce an article of manufacture which implements the functions specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method of detecting a skin condition according to one embodiment of the invention, as shown in FIG. 3, may include employing a multiband hyperspectral sensor to obtain multi-spectral data at operation 200 and employing the multi-spectral data to map constitutive skin parameters to corresponding spectral signatures via a forward model that enables generation of a set of samples including a plurality of parameters mapped to a plurality of spectral signatures at operation 210. The method may further include utilizing the set of samples to employ machine learning to generate an inverse model to enable mapping of a spectral signature of skin of a patient to corresponding skin parameters at operation 220, estimating constitutive skin parameters of the skin of the patient based on the inverse model at operation 230, and determining a distribution of the constitutive parameters for one or more skin locations at operation 240.

In some embodiments, additional optional operations some examples of which are shown in dashed lines in FIG. 3) may be included or the operations described above may be modified or augmented. Each of the additional operations, modification or augmentations may be practiced in combination with the operations above and/or in combination with each other. Thus, some, all or none of the additional operations, modification or augmentations may be utilized in some embodiments. In an example embodiment, the method may further include storing first data indicative of the distribution of constitutive parameters in association with the patient and a first date of capture of the spectral signature of the skin of the patient at operation 250. In an example embodiment, the method may further include capturing another spectral signature at a second date, and comparing second data indicative of the distribution of constitutive parameters in association with the patient at the second date with the first data to determine anomaly detection based on changes in the first and second data at operation 260. Instead of, additionally or alternatively to operations 250 and 260, the method may further include comparing data indicative of a distribution in one area of the skin of the patient to data indicative of a distribution of constitutive parameters in another area of the skin of the patient to determine anomaly detection based on the comparison at operation 270. In such an example, the comparison may be conducted in real-time while the skin of the patient is being examined. In some embodiments, the inverse model is generated via a support vector regression (SVR) algorithm or a k-nearest neighbors (k-NN) regression algorithm. In an example embodiment, the distribution of constitutive parameters may be determined by determining distribution relative to constitutive parameters including melanosome level, collagen level, blood oxygenation, blood level, dermal depth, or subcutaneous tissue reflectance.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A detection system comprising:
   a multiband hyperspectral sensor configured to obtain spectral signatures; and
   a parametric analyzer including processing circuitry configured to:
   employ a physics-based model that maps an input vector space including biological parameters to an output vector having spectral components of corresponding biological parameters to map constitutive skin parameters to corresponding spectral signatures via a forward model, the forward model enabling generation of a set of samples including a plurality of parameters mapped to a plurality of spectral signatures;
   utilize the set of samples to employ machine learning to generate an inverse model to enable mapping of a spectral signature of skin of a patient to corresponding skin parameters;
   estimate constitutive skin parameters of the skin of the patient based on the inverse model and a measured spectral signature; and
   determine a distribution of the constitutive parameters for one or more skin locations to perform diagnosis.

2. The detection system of claim 1, wherein the processing circuitry is configured to determine the distribution of constitutive parameters by determining distribution relative to constitutive parameters including melanosome level, collagen level, blood oxygenation, blood level, dermal depth, or subcutaneous tissue reflectance.

3. The detection system of claim 1, wherein the inverse model is generated via a support vector regression (SVR) algorithm.

4. The detection system of claim 1, wherein the inverse model is generated via a k-nearest neighbors (k-NN) regression algorithm.

5. The detection system of claim 1, wherein the processing circuitry is further configured to store first data indicative of the distribution of constitutive parameters in association with the patient and a first date of capture of the spectral signature of the skin of the patient.

6. The detection system of claim 5, wherein the processing circuitry is further configured to capture another spectral signature at a second date, and compare second data indicative of the distribution of constitutive parameters in association with the patient at the second date with the first data to determine anomaly detection based on changes in the first and second data.

7. The detection system of claim 1, wherein the processing circuitry is further configured to compare data indicative of a distribution in one area of the skin of the patient to data indicative of a distribution of constitutive parameters in another area of the skin of the patient to determine anomaly detection based on the comparison.

8. The detection system of claim 1, wherein the comparison is conducted in real-time while the skin of the patient is being examined.

9. A method comprising:
   employing a multiband hyperspectral sensor to obtain spectral signatures;
   employing a physics-based model that maps an input vector space including biological parameters to an output vector having spectral components of corresponding biological parameters to map constitutive skin parameters to corresponding spectral signatures via a forward model, the forward model enabling generation of a set of samples including a plurality of parameters mapped to a plurality of spectral signatures;
   utilizing the set of samples to employ machine learning to generate an inverse model to enable mapping of a spectral signature of skin of a patient to corresponding skin parameters;
   estimating, via processing circuitry, constitutive skin parameters of the skin of the patient based on the inverse model and a measured spectral signature; and
   determining a distribution of the constitutive parameters for one or more skin locations to perform diagnosis.

10. The method of claim 9, wherein determining the distribution of constitutive parameters comprises determining distribution relative to constitutive parameters including melanosome level, collagen level, blood oxygenation, blood level, dermal depth, or subcutaneous tissue reflectance.

11. The method of claim 9, wherein the inverse model is generated via a support vector regression (SVR) algorithm.

12. The method of claim 9, wherein the inverse model is generated via a k-nearest neighbors (k-NN) regression algorithm.

13. The method of claim 9, further comprising storing first data indicative of the distribution of constitutive parameters in association with the patient and a first date of capture of the spectral signature of the skin of the patient.

14. The method of claim 13, further comprising capturing another spectral signature at a second date, and comparing second data indicative of the distribution of constitutive parameters in association with the patient at the second date with the first data to determine anomaly detection based on changes in the first and second data.

15. The method of claim 9, further comprising comparing data indicative of a distribution in one area of the skin of the patient to data indicative of a distribution of constitutive parameters in another area of the skin of the patient to determine anomaly detection based on the comparison.

16. The method of claim 15, wherein the comparison is conducted in real-time while the skin of the patient is being examined.

17. A computer program product comprising a non-transitory computer-readable storage medium having computer-executable program code instructions stored therein, the computer-executable program code instructions comprising program code instructions for:
   employing a multiband hyperspectral sensor to obtain spectral signatures;
   employing a physics-based model that maps an input vector space including biological parameters to an output vector having spectral components of corresponding biological parameters to map constitutive skin parameters to corresponding spectral signatures via a forward model, the forward model enabling generation of a set of samples including a plurality of parameters mapped to a plurality of spectral signatures;
   utilizing the set of samples to employ machine learning to generate an inverse model to enable mapping of a spectral signature of skin of a patient to corresponding skin parameters;
   estimating, via processing circuitry, constitutive skin parameters of the skin of the patient based on the inverse model and a measured spectral signature; and determining a distribution of the constitutive parameters for one or more skin locations to perform diagnosis.

18. The computer program product of claim 17, wherein program code instructions for determining the distribution of constitutive parameters include instructions for determining distribution relative to constitutive parameters including melanosome level, collagen level, blood oxygenation, blood level, dermal depth, or subcutaneous tissue reflectance.

19. The computer program product of claim 17, wherein the inverse model is generated via a support vector regression (SVR) algorithm or a k-nearest neighbors (k-NN) regression algorithm.

20. The computer program product of claim 17, further comprising program code instructions for storing data indicative of the distribution of constitutive parameters in association with the patient and a date of capture of the spectral signature of the skin of the patient.

* * * * *